(12) United States Patent
Rodgers et al.

(10) Patent No.: US 11,583,123 B2
(45) Date of Patent: Feb. 21, 2023

(54) PARCEL STORAGE ASSEMBLY

(71) Applicants: Thomas Rodgers, Gulfport, FL (US); John Nash, Gulfport, FL (US)

(72) Inventors: Thomas Rodgers, Gulfport, FL (US); John Nash, Gulfport, FL (US)

(*) Notice: Subject to any disclaimer, the term of this patent is extended or adjusted under 35 U.S.C. 154(b) by 397 days.

(21) Appl. No.: 16/942,446

(22) Filed: Jul. 29, 2020

(65) Prior Publication Data

US 2022/0031104 A1    Feb. 3, 2022

(51) Int. Cl.
  *G07C 9/00*   (2020.01)
  *A47G 29/14*  (2006.01)
  *A61L 2/10*   (2006.01)
  *A47G 29/20*  (2006.01)
  *A47G 29/30*  (2006.01)

(52) U.S. Cl.
  CPC ........... *A47G 29/141* (2013.01); *A47G 29/20* (2013.01); *A47G 29/30* (2013.01); *A61L 2/10* (2013.01); *A47G 2029/146* (2013.01); *A47G 2029/147* (2013.01)

(58) Field of Classification Search
  None
  See application file for complete search history.

(56) References Cited

U.S. PATENT DOCUMENTS

| | | |
|---|---|---|
| D445,234 S | 7/2001 | Isaacs |
| 6,612,489 B2 | 9/2003 | McCormick |
| 7,175,071 B1 | 2/2007 | Slagle |
| 9,619,955 B2 | 4/2017 | Eichenblatt |
| 9,861,221 B2 * | 1/2018 | Jiang .................... A47G 29/141 |
| 2012/0158606 A1 | 6/2012 | Moudy |
| 2017/0124510 A1 | 5/2017 | Caterino |
| 2017/0251856 A1 | 9/2017 | Schaible |

FOREIGN PATENT DOCUMENTS

WO    WO20170790006    5/2017

* cited by examiner

*Primary Examiner* — K. Wong (57) ABSTRACT

A parcel storage assembly for remotely securing a parcel delivery includes a box that is positionable adjacent to an entry of a building to be accessible to a parcel delivery person. A lid is hingedly coupled to the box for opening and closing the box. A locking unit is coupled to the box and the locking unit engages the lid when the locking unit is turned on to inhibit the lid from is opened. The locking unit is in wireless communication with a personal electronic device to facilitate a user to remotely lock and unlock the box. A light emitter is coupled to the box to kill bacteria and sterilizing the parcel delivered by the parcel delivery person. A cooler is positionable within the box for receiving a food delivery positioned therein.

10 Claims, 7 Drawing Sheets

PARCEL STORAGE ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to storage devices and more particularly pertains to a new storage device for remotely securing a parcel delivery.

(2) Description of Related Art Including Information Disclosed Under 37 CFR 1.97 and 1.98

The prior art relates to storage devices including a variety of parcel lock boxes that each has a keypad for entering a numeric code to open the parcel lock boxes. The prior art discloses a system for facilitating secure package delivery that includes digital imagery and an input device for entering package information. The prior art discloses a variety of package storage devices that include electronic means of package verification for unlocking a storage box. The prior art also discloses an ornamental design for a storage box.

BRIEF SUMMARY OF THE INVENTION

An embodiment of the disclosure meets the needs presented above by generally comprising a box that is positionable adjacent to an entry of a building to be accessible to a parcel delivery person. A lid is hingedly coupled to the box for opening and closing the box. A locking unit is coupled to the box and the locking unit engages the lid when the locking unit is turned on to inhibit the lid from is opened. The locking unit is in wireless communication with a personal electronic device to facilitate a user to remotely lock and unlock the box. A light emitter is coupled to the box to kill bacteria and sterilizing the parcel delivered by the parcel delivery person. A cooler is positionable within the box for receiving a food delivery positioned therein.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
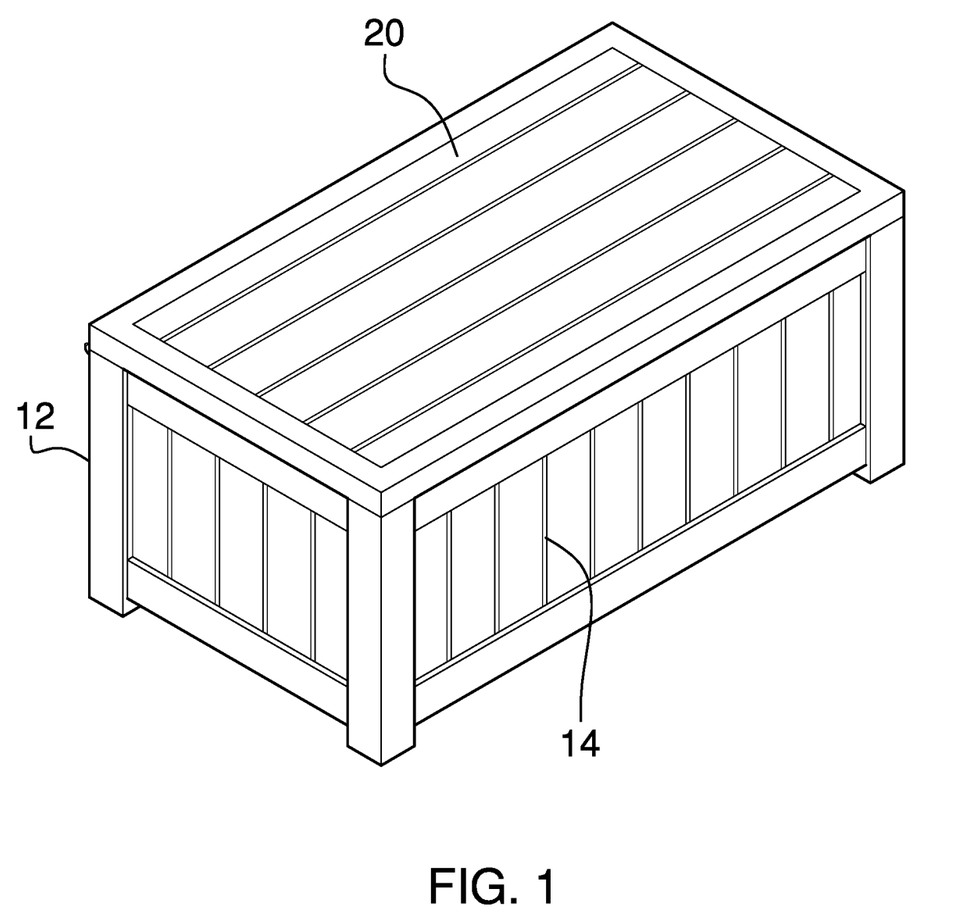
FIG. 1 is a perspective view of a parcel storage assembly according to an embodiment of the disclosure.
Figure 2:
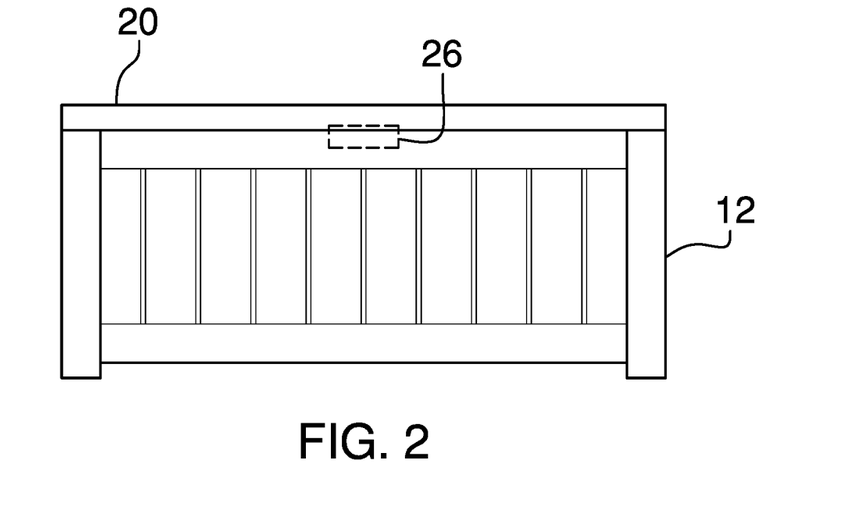
FIG. 2 is a front phantom view of an embodiment of the disclosure.
Figure 3:
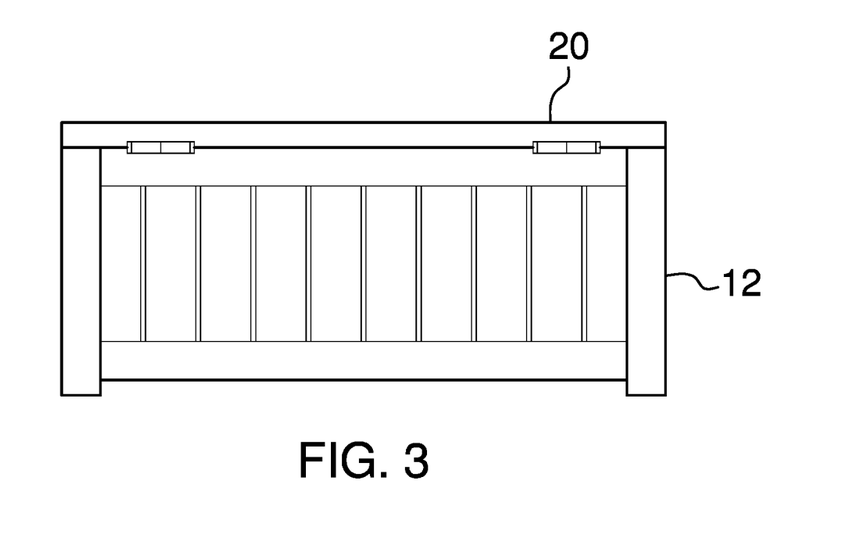
FIG. 3 is a back view of an embodiment of the disclosure.
Figure 4:
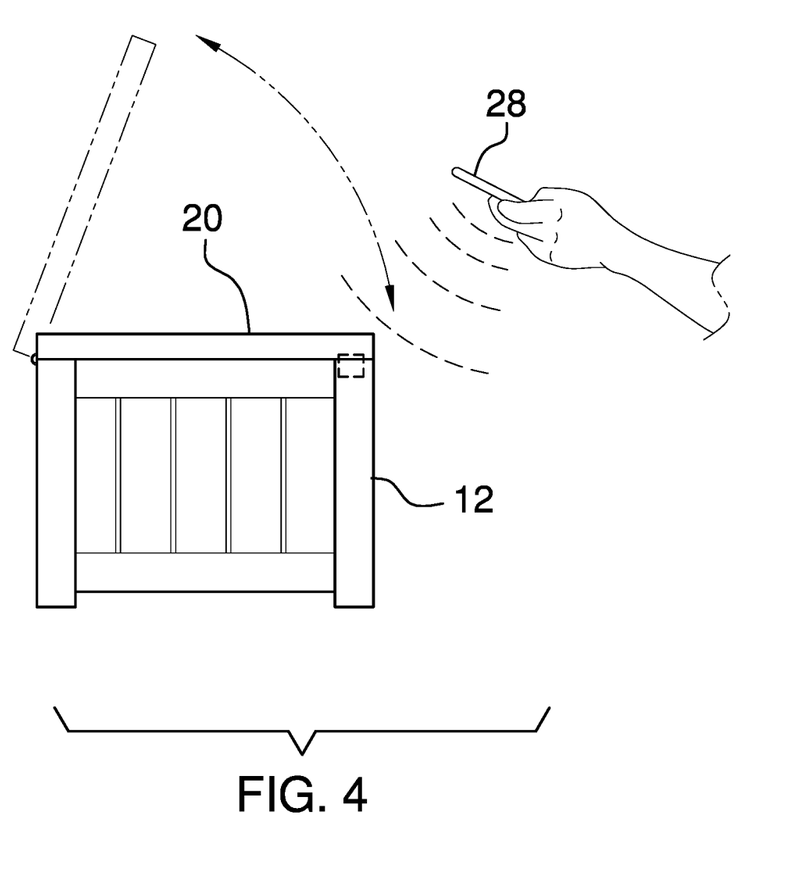
FIG. 4 is a right side view of an embodiment of the disclosure.
Figure 5:
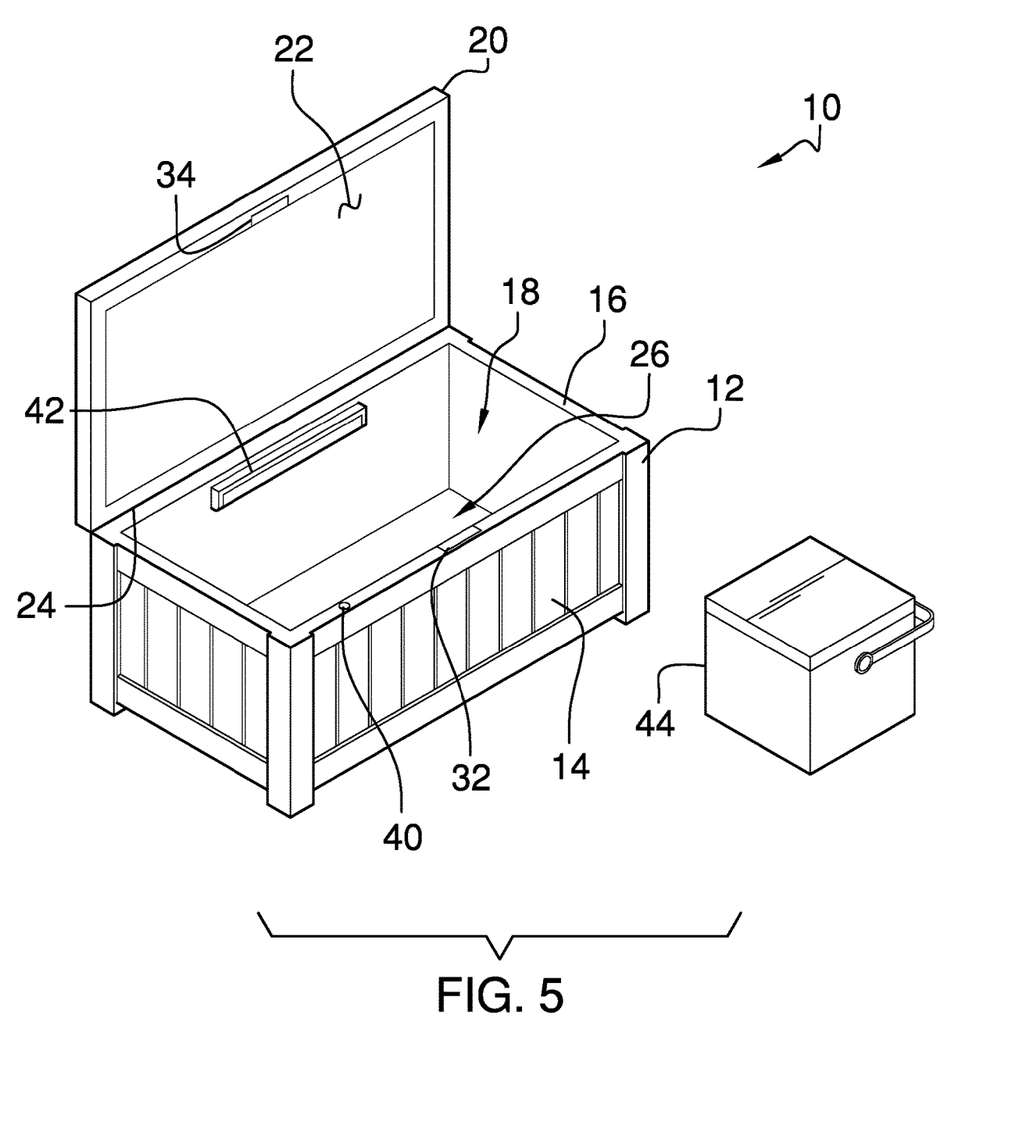
FIG. 5 is a top perspective view of an embodiment of the disclosure.
Figure 6:
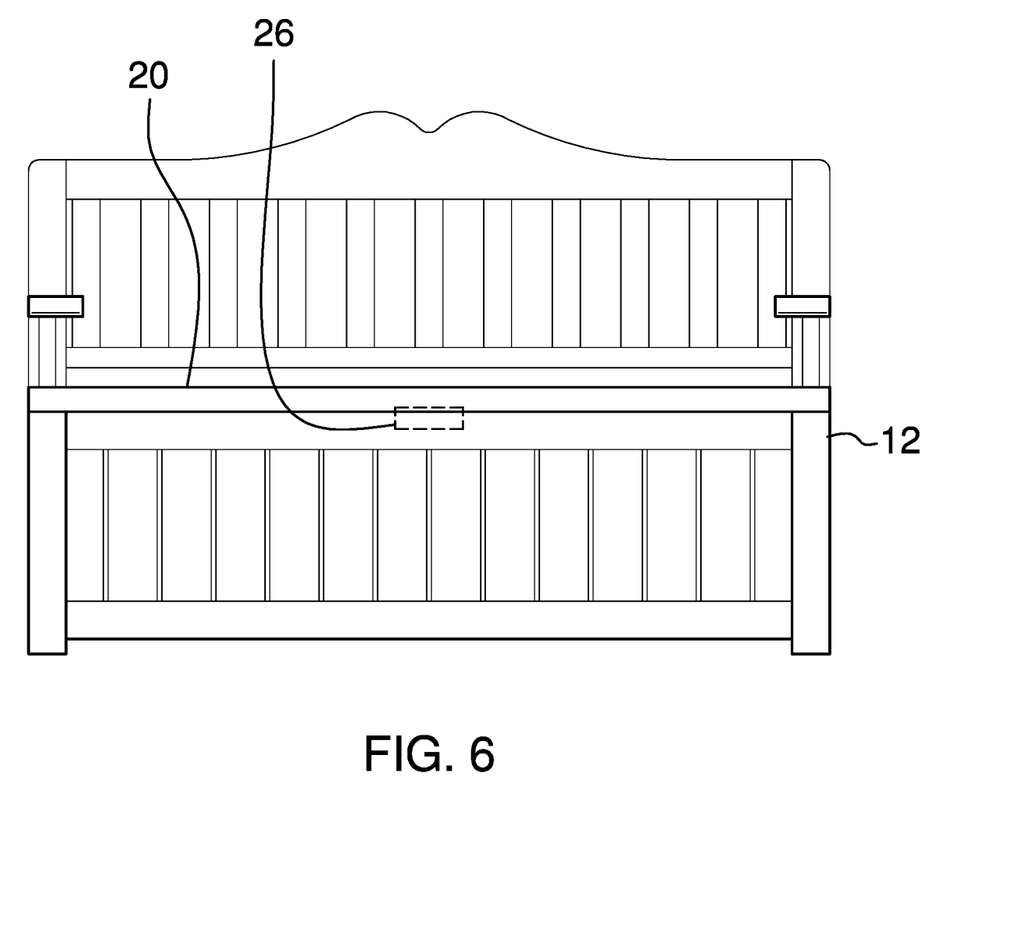
FIG. 6 is a front view of an embodiment of the disclosure.
Figure 7:
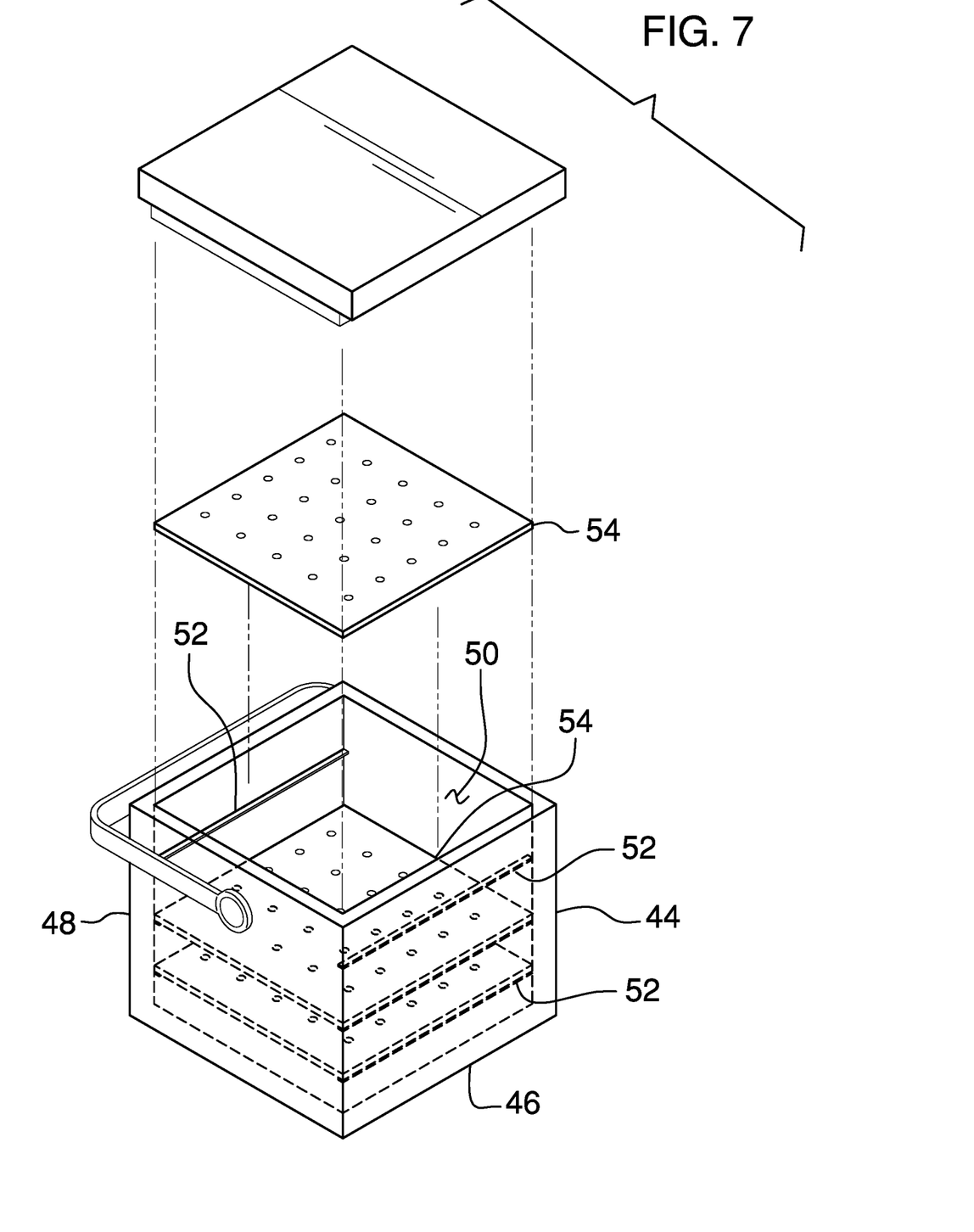
FIG. 7 is an exploded perspective view of a cooler of an embodiment of the disclosure.
Figure 8:
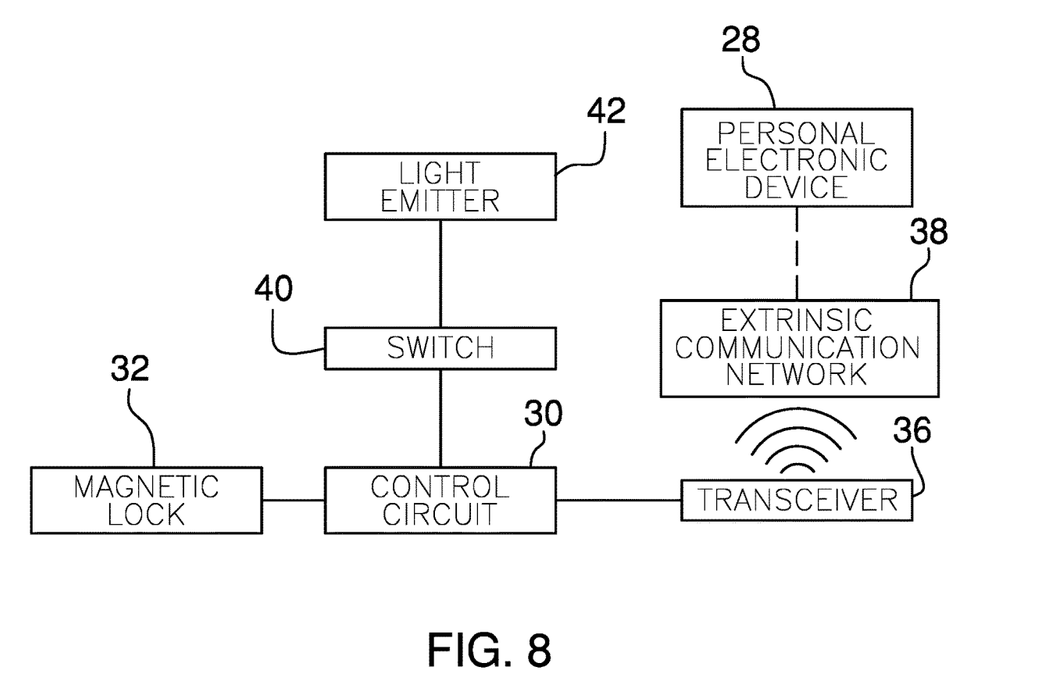
FIG. 8 is a schematic view of an embodiment of the disclosure.

With reference now to the drawings, and in particular to FIGS. 1 through 8 thereof, a new storage device embodying the principles and concepts of an embodiment of the disclosure and generally designated by the reference numeral 10 will be described.

As best illustrated in FIGS. 1 through 8, the parcel storage assembly 10 generally comprises a box 12 is positionable adjacent to an entry of a building, such as a residence or other occupied building. In this way the box 12 is accessible to a parcel delivery person. The box 12 has an outer wall 14 and the outer wall 14 has a top edge 16 defining an opening 18 into the box 12. A lid 20 is hingedly coupled to the box 12 for opening 18 and closing the box 12. The lid 20 has a lower surface 22 and a rear edge 24. The rear edge 24 is hingedly coupled to the top edge 16 of the outer wall 14 of the box 12 and the lower surface 22 rests on the top edge 16 when the lid 20 is closed. As is most clearly shown in FIG. 6, the box 12 may be structured to have the ornamental appearance of a bench or other similar article of furniture for sitting.

A locking unit 26 is provided and the locking unit 26 is coupled to the box 12. The locking unit 26 engages the lid 20 when the locking unit 26 is turned on to inhibit the lid 20 from being opened. Conversely, the locking unit 26 disengages the lid 20 when the locking unit 26 is turned off thereby facilitating the lid 20 to be opened. The locking unit 26 is in wireless communication with a personal electronic device 28, such as a smart phone or the like. In this way the locking unit 26 can be remotely turned on and off by a user.

Additionally, the locking unit 26 is in communication with a surveillance camera 28 of the building. In this way the locking unit 26 can communicate imagery from the surveillance camera 28 to the personal electronic device 28 to facilitate the user to verify the identity of the parcel delivery person.

The locking unit 26 comprises a control circuit 30 that is coupled to the box 12. The control circuit 30 receives a lock input and an unlock input. Additionally, the control circuit 30 is in electrical communication with the surveillance camera 28. The control circuit 30 is electrically coupled to a power source comprising an electrical system of the building.

The locking unit 26 includes a magnetic lock 32 that is coupled to the box 12. The magnetic lock 32 includes an engagement 34 that is coupled to the lower surface 22 of the lid 20. The magnetic lock 32 is electrically coupled to the control circuit 30. The magnetic lock 32 magnetically engages the engagement 34 when the control circuit 30 receives the lock input. In this way the lid 20 from is inhibited from being opened. The magnetic lock 32 magnetically disengages the engagement 34 when the control circuit 30 receives the unlock input to facilitate the lid 20 to be opened. The magnetic lock 32 may an electromagnet that produces a magnetic field of sufficient strength to inhibit a human being from opening the lid 20.

The locking unit 26 includes a transceiver 36 that is coupled to the box 12 and the transceiver 36 is electrically coupled to the control circuit 30. The transceiver 36 is in wireless communication with an extrinsic communication network 38, such as a cellular phone network or the like. In this way the transceiver 36 can communicate with the personal electronic device 28. The transceiver 36 may comprise a radio frequency transceiver or the like.

A switch 40 is coupled to the box 12 and the switch 40 is electrically coupled to the control circuit 30. The switch 40 is turned on when the lid 20 is closed and the switch 40 is turned off when the lid 20 is opened. A light emitter 42 is coupled to the box 12 and the light emitter 42 emits light in the ultraviolet spectrum. In this way the light emitter 42 can kill bacteria. The light emitter 42 is turned on when the lid 20 is opened to sterilize the parcel being delivered by the parcel delivery person. The light emitter 42 is positioned in an interior of the box 12 and the light emitter 42 is electrically coupled to the control circuit 30. The light emitter 42 is turned on when the switch 40 is turned on and the light emitter 42 is turned off when the switch 40 is turned off. The light emitter 42 may comprise fluorescent light bulb that emits ultraviolet light.

A cooler 44 is provided and the cooler 44 is positionable within the box 12 for receiving a food delivery. The cooler 44 is comprised of a thermally insulating material to retain the food delivery at a desired temperature. The cooler 44 has a bottom wall 46 and an outside wall 48 extending upwardly therefrom. The outside wall 48 has an inner surface 50 and a plurality of rails 52 is coupled to the inner surface 50. Each of the rails 52 is horizontally oriented and the rails 52 are spaced apart from each other and are vertically distributed on the inner surface 50. A plurality of trays 54 is provided and each of the trays 54 is perforated. In this way each of the trays 54 can pass air therethrough. Each of the trays 54 is positionable on a respective pair of rails 52 in the cooler 44 to vertically stack food items in the cooler 44.

In use, the user views the footage from the surveillance camera 28 when the parcel delivery person approaches the box 12 to deliver the parcel. In this way the user can visually identify the parcel delivery person. The user unlocks the box 12 with the personal electronic device 28 thereby facilitating the parcel delivery person to place the parcel in the box 12. The user locks the box 12 with the personal electronic device 28 when the parcel delivery person closes the lid 20. In this way the parcel is secured until the user is able to retrieve the parcel from the box 12. Additionally, the cooler 44 facilitates a food delivery to be secured in the box 12 until the user can retrieve the food delivery.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A parcel storage assembly for securely storing a delivered parcel for subsequent retrieval by an authorized user, said assembly comprising:
   a box being positionable adjacent to an entry of a building wherein said box is configured to be accessible to a parcel delivery person;
   a lid being hingedly coupled to said box for opening and closing said box;
   a locking unit being coupled to said box, said locking unit engaging said lid when said locking unit is turned on to inhibit said lid from being opened, said locking unit disengaging said lid when said locking unit is turned off thereby facilitating said lid to be opened, said locking unit being in wireless communication with a personal electronic device wherein said locking unit is configured to be remotely turned on and off by a user, said locking unit being in communication with a surveillance camera of the building wherein said locking unit is configured to communicate imagery from the surveillance camera to the personal electronic device to facilitate the user to verify the identity of the parcel delivery person;
   a light emitter being coupled to said box, said light emitter emitting light in the ultraviolet spectrum wherein said light emitter is configured to kill bacteria, said light emitter being turned on when said lid is opened wherein said light emitter is configured to sterilize the parcel being delivered by the parcel delivery person; and
   a cooler being positionable within said box wherein said cooler is configured to have a food delivery positioned therein, said cooler being comprised of a thermally insulating material wherein said cooler is configured to retain the food delivery at a desired temperature.

2. The assembly according to claim 1, wherein:
said box has an outer wall, said outer wall having a top edge defining an opening into said box; and
said lid has a lower surface and a rear edge, said rear edge being hingedly coupled to said top edge of said outer wall of said box, said lower surface resting on said top edge when said lid is closed.

3. The assembly according to claim 1, wherein said locking unit comprises a control circuit being coupled to said box, said control circuit receiving a lock input and an unlock input, said control circuit being in electrical communication with the surveillance camera, said control circuit being electrically coupled to a power source comprising an electrical system of the building.

4. The assembly according to claim 3, wherein said locking unit includes a magnetic lock being coupled to said box, said magnetic lock including an engagement being coupled to a lower surface of said lid, said magnetic lock being electrically coupled to said control circuit, said magnetic lock magnetically engaging said engagement when said control circuit receives said lock input to inhibit said lid from being opened, said magnetic lock magnetically disengaging said engagement when said control circuit receives said unlock input to facilitate said lid to be opened.

5. The assembly according to claim 3, wherein said locking unit includes a transceiver being coupled to said box, said transceiver being electrically coupled to said control circuit, said transceiver being in wireless communication with an extrinsic communication network thereby facilitating said transceiver to communicate with the personal electronic device.

6. The assembly according to claim 3, further comprising a switch being coupled to said box, said switch being electrically coupled to said control circuit, said switch being turned on when said lid is closed, said switch being turned off when said lid is opened.

7. The assembly according to claim 6, wherein said light emitter is positioned in an interior of said box, said light emitter being electrically coupled to said control circuit, said light emitter being turned on when said switch is turned on, said light emitter being turned off when said switch is turned off.

8. The assembly according to claim 1, wherein said cooler has a bottom wall and an outside wall extending upwardly therefrom, said outside wall having an inner surface, said inner surface having a plurality of rails being coupled thereto, each of said rails being horizontally oriented, said plurality of rails being spaced apart from each other and being vertically distributed on said inner surface.

9. The assembly according to claim 8, further comprising a plurality of trays, each of said trays being perforated wherein each of said trays is configured to pass air therethrough, each of said trays being positionable on a respective pair of rails in said cooler wherein each of said trays is configured to vertically stack food items in said cooler.

10. A parcel storage assembly for securely storing a delivered parcel for subsequent retrieval by an authorized user, said assembly comprising:
a box being positionable adjacent to an entry of a building wherein said box is configured to be accessible to a parcel delivery person, said box having an outer wall, said outer wall having a top edge defining an opening into said box;
a lid being hingedly coupled to said box for opening and closing said box, said lid having a lower surface and a rear edge, said rear edge being hingedly coupled to said top edge of said outer wall of said box, said lower surface resting on said top edge when said lid is closed;
a locking unit being coupled to said box, said locking unit engaging said lid when said locking unit is turned on to inhibit said lid from being opened, said locking unit disengaging said lid when said locking unit is turned off thereby facilitating said lid to be opened, said locking unit being in wireless communication with a personal electronic device wherein said locking unit is configured to be remotely turned on and off by a user, said locking unit being in communication with a surveillance camera of the building wherein said locking unit is configured to communicate imagery from the surveillance camera to the personal electronic device to facilitate the user to verify the identity of the parcel delivery person, said locking unit comprising:
a control circuit being coupled to said box, said control circuit receiving a lock input and an unlock input, said control circuit being in electrical communication with the surveillance camera, said control circuit being electrically coupled to a power source comprising an electrical system of the building;
a magnetic lock being coupled to said box, said magnetic lock including an engagement being coupled to said lower surface of said lid, said magnetic lock being electrically coupled to said control circuit, said magnetic lock magnetically engaging said engagement when said control circuit receives said lock input to inhibit said lid from being opened, said magnetic lock magnetically disengaging said engagement when said control circuit receives said unlock input to facilitate said lid to be opened; and
a transceiver being coupled to said box, said transceiver being electrically coupled to said control circuit, said transceiver being in wireless communication with an extrinsic communication network thereby facilitating said transceiver to communicate with the personal electronic device;
a switch being coupled to said box, said switch being electrically coupled to said control circuit, said switch being turned on when said lid is closed, said switch being turned off when said lid is opened;
a light emitter being coupled to said box, said light emitter emitting light in the ultraviolet spectrum wherein said light emitter is configured to kill bacteria, said light emitter being turned on when said lid is opened wherein said light emitter is configured to sterilize the parcel being delivered by the parcel delivery person, said light emitter being positioned in an interior of said box, said light emitter being electrically coupled to said control circuit, said light emitter being turned on when said switch is turned on, said light emitter being turned off when said switch is turned off; and
a cooler being positionable within said box wherein said cooler is configured to have a food delivery positioned therein, said cooler being comprised of a thermally insulating material wherein said cooler is configured to retain the food delivery at a desired temperature, said cooler having a bottom wall and an outside wall extending upwardly therefrom, said outside wall having an inner surface, said inner surface having a plurality of rails being coupled thereto, each of said rails being horizontally oriented, said plurality of rails being spaced apart from each other and being vertically distributed on said inner surface; and
a plurality of trays, each of said trays being perforated wherein each of said trays is configured to pass air therethrough, each of said trays being positionable on a respective pair of rails in said cooler wherein each of said trays is configured to vertically stack food items in said cooler.

\* \* \* \* \*